United States Patent
Feller, III

(10) Patent No.: US 9,339,368 B2
(45) Date of Patent: May 17, 2016

(54) THIN FILM MEDICAL DEVICE AND DELIVERY SYSTEM

(75) Inventor: Frederick Feller, III, Coral Springs, FL (US)

(73) Assignee: Cordis Corporation, Fremont, CA (US)

(*) Notice: Subject to any disclaimer, the term of this patent is extended or adjusted under 35 U.S.C. 154(b) by 885 days.

(21) Appl. No.: 12/577,226

(22) Filed: Oct. 12, 2009

(65) Prior Publication Data

US 2010/0030320 A1 Feb. 4, 2010

Related U.S. Application Data

(62) Division of application No. 11/237,362, filed on Sep. 28, 2005, now abandoned.

(60) Provisional application No. 60/614,012, filed on Sep. 28, 2004.

(51) Int. Cl.
*A61F 2/06* (2013.01)
*A61F 2/07* (2013.01)
(Continued)

(52) U.S. Cl.
CPC .............. *A61F 2/07* (2013.01); *A61B 17/12022* (2013.01); *A61B 17/12118* (2013.01); *A61F 2/95* (2013.01); *A61F 2/966* (2013.01); *A61B 2017/00867* (2013.01);
(Continued)

(58) Field of Classification Search
CPC ................... A61B 17/12022; A61B 17/12118; A61B 2017/00867; A61B 2017/1205; A61F 2002/075; A61F 2002/823; A61F 2002/9583; A61F 2/07; A61F 2/89; A61F 2/95; A61F 2/958; A61F 2/966

USPC ............. 623/1.11, 1.12, 1.17, 1.18, 1.44
See application file for complete search history.

(56) References Cited

U.S. PATENT DOCUMENTS 5,163,952 A * 11/1992 Froix ........................... 623/1.18
5,279,596 A    1/1994 Castaneda et al.
(Continued)

FOREIGN PATENT DOCUMENTS

EP       941716 A2    9/1999
EP      1435221 A1    7/2004
(Continued)

OTHER PUBLICATIONS

Japanese Notification of Reasons for Refusal mailed Jul. 5, 2011 from corresponding Japanese Patent Application No. 2007-533777.
(Continued)

*Primary Examiner* — Julian W Woo

(57) ABSTRACT

The present invention relates to a delivery system for an intraluminal thin film medical device particularly well suited for occlusion of an aneurysm, vessel side branch or dissection of a body lumen or duct, such as an artery or vein. The delivery system has an outer sheath attached along the distal end of a relatively long and flexible tubular shaft. The outer sheath is capable of constraining the thin film medical device in a longitudinally stretched position, and subsequently being retracted relative to the flexible tubular shaft to release the thin film medical device from the constrained longitudinally stretched position. The delivery system may additionally have a mechanical expansion catheter substantially coaxial too, and slideably engaged within, the outer sheath and an inner lumen substantially coaxial to the outer sheath and incorporated into the flexible tubular shaft.

11 Claims, 3 Drawing Sheets

(51) Int. Cl.
*A61B 17/12* (2006.01)
*A61F 2/95* (2013.01)
*A61F 2/966* (2013.01)
 A61B 17/00 (2006.01)
 A61F 2/958 (2013.01)
 A61F 2/82 (2013.01)
 A61F 2/89 (2013.01)

(52) U.S. Cl.
CPC .......... *A61B 2017/1205* (2013.01); *A61F 2/89* (2013.01); *A61F 2/958* (2013.01); *A61F 2002/075* (2013.01); *A61F 2002/823* (2013.01); *A61F 2002/9583* (2013.01)

(56) References Cited

U.S. PATENT DOCUMENTS

| | | | |
|---|---|---|---|
| 5,304,197 A | 4/1994 | Pinchuk et al. | |
| 5,370,615 A | 12/1994 | Johnson | |
| 5,713,917 A | 2/1998 | Leonhardt et al. | |
| 5,735,897 A * | 4/1998 | Buirge | 623/1.44 |
| 5,800,517 A * | 9/1998 | Anderson et al. | 623/1.12 |
| 5,824,049 A * | 10/1998 | Ragheb et al. | 623/1.44 |
| 5,824,053 A | 10/1998 | Khosravi et al. | |
| 5,948,191 A * | 9/1999 | Solovay | 623/1.11 |
| 5,980,531 A | 11/1999 | Goodin et al. | |
| 6,086,610 A * | 7/2000 | Duerig et al. | 623/1.18 |
| 6,280,411 B1 | 8/2001 | Lennox | |
| 6,425,898 B1 | 7/2002 | Wilson et al. | |
| 6,458,152 B1 | 10/2002 | Khosravi et al. | |
| 6,461,370 B1 | 10/2002 | Gray et al. | |
| 6,491,720 B1 * | 12/2002 | Vallana et al. | 623/1.44 |
| 6,849,085 B2 * | 2/2005 | Marton | 623/1.44 |
| 2001/0032013 A1 * | 10/2001 | Marton | 623/1.15 |
| 2001/0034548 A1 | 10/2001 | Vrba et al. | |
| 2002/0029075 A1 | 3/2002 | Leonhardt | |
| 2002/0103525 A1 | 8/2002 | Cummings | |
| 2003/0028246 A1 | 2/2003 | Palmaz et al. | |
| 2003/0130718 A1 | 7/2003 | Palmas et al. | |
| 2003/0176910 A1 | 9/2003 | Vrba et al. | |
| 2003/0236565 A1 * | 12/2003 | DiMatteo et al. | 623/1.12 |
| 2005/0021002 A1 | 1/2005 | Deckman et al. | |

FOREIGN PATENT DOCUMENTS

| | | |
|---|---|---|
| EP | 1508313 B1 | 12/2008 |
| EP | 1793765 B1 | 3/2011 |
| JP | 5269197 A | 10/1993 |
| JP | 11313893 A | 11/1999 |
| JP | 2002534195 T | 10/2002 |
| WO | WO 0004204 A1 | 1/2000 |
| WO | WO 0041525 A2 | 7/2000 |
| WO | WO 02/102284 A2 | 12/2002 |
| WO | WO 03099168 A2 | 12/2003 |
| WO | WO 2004045673 A2 | 6/2004 |
| WO | WO 2006037084 A1 | 4/2006 |

OTHER PUBLICATIONS

Opposition by Abbott Laboratories Vascular Enterprises Limited mailed Dec. 23, 2011 in corresponding European Patent No. 1793765.

\* cited by examiner

THIN FILM MEDICAL DEVICE AND DELIVERY SYSTEM

CROSS REFERENCE TO RELATED APPLICATIONS

This application is a Divisional filed under 35 USC §121 of U.S. patent application Ser. No. 11/237,362 filed Sep. 28, 2005, now abandoned, which claims the benefit of and priority to U.S. Provisional Application No. 60/614,012, filed Sep. 28, 2004, now expired.

FIELD OF THE INVENTION

The present invention relates to a thin film medical device, and in particular to an intraluminal thin film medical device and delivery system. This medical device and delivery system are particularly well suited for occlusion of an aneurysm, vessel side branch or dissection of a body lumen or duct, such as an artery or vein.

BACKGROUND OF THE INVENTION

There are many instances when it may be desirable to permanently occlude a vessel in the human body. Examples of when permanent occlusion of a vessel might be desirable include: occlusion of an aneurysm or side branch vessel; therapeutic occlusion, or embolization, of the renal artery; occlusion of a Blalock-Taussig Shunt; pulmonary arteriovenous fistulae and transjugular intrahepatic stent shunt occlusion; some non-vascular applications, such as therapeutic ureteric occlusion; and the occlusion of vessels feeding large cancerous tumors.

In the past, certain coiled stents, stent grafts or detachable balloons have been utilized for providing permanent occlusion of vessels. Stent-grafts are essentially endoluminal stents with a discrete covering on either or both of the luminal and abluminal surfaces of the stent that occludes the open spaces, or interstices, between adjacent structural members of the endoluminal stent. It is known in the art to fabricate stent-grafts by covering the stent with endogenous vein or a synthetic material, such as woven polyester known as DACRON, or with expanded polytetrafluoroethylene. Additionally, it is known in the art to cover the stent with a biological material, such as a xenograft or collagen.

There are certain problems associated with coiled stents, including, migration of the coiled stent within the vessel to be occluded, perforation of the vessel by the coiled stent, and failure to completely thrombose, or occlude, the vessel. Another disadvantage associated with such coiled stents is that the vessel may not be immediately occluded following placement in the vessel. Disadvantages associated with detachable occlusion balloons include premature detachment with distal embolization, or occlusion, and they are believed to require a longer period of time for the user of the device to learn how to properly use such detachable occlusion balloons.

In addition to vessel occlusion, conventional graft type intraluminal medical devices are frequently used post-angioplasty in order to provide a structural support for a blood vessel and reduce the incidence of restenosis following percutaneous balloon angioplasty. A principal example are endovascular stents which are introduced to a site of disease or trauma within the body's vasculature from an introductory location remote from the disease or trauma site using an introductory catheter, passed through the vasculature communicating between the remote introductory location and the disease or trauma site, and released from the introductory catheter at the disease or trauma site to maintain patency of the blood vessel at the site of disease or trauma. Stent-grafts are delivered and deployed under similar circumstances and are utilized to maintain patency of an anatomic passageway, for example, by reducing restenosis following angioplasty, or when used to exclude an aneurysm, such as in aortic aneurysm exclusion applications.

While these medical devices have specific advantages, their overall size, in particular the diameter and delivery profile, are significant disadvantages that render these devices prohibitive for certain uses. Another significant disadvantage is the limited flexibility these devices have for navigating paths through small and/or tortuous vessels. As such, they may not be desirable for many small diameter vessel applications, for example neurovascular vessels.

What is needed is a medical device capable of occluding various parts of a vessel that can assume a reduced diameter and delivery profile.

SUMMARY OF THE INVENTION

The present invention relates to a delivery system for an intraluminal thin film medical device particularly well suited for occlusion of an aneurysm, vessel side branch or dissection of a body lumen or duct, such as an artery or vein.

In one embodiment of the invention, the delivery system comprises an outer sheath attached along the distal end of a relatively long and flexible tubular shaft. The outer sheath is capable of constraining the thin film medical device in a longitudinally stretched position, and subsequently being retracted relative to the flexible tubular shaft to release the thin film medical device from the constrained longitudinally stretched position. The delivery system further comprises a secondary sheath substantially coaxial too, and slideably engaged within, the outer sheath. The secondary sheath is capable of restraining the self-expanding support structure in a radially constrained position, and subsequently being retracted to release the self-expanding support structure from the radially constrained position. An inner lumen is substantially coaxial to the outer sheath and incorporated into the flexible tubular shaft.

In another embodiment of the invention, the delivery system is configured for deploying a self-supporting thin film medical device in a body lumen. The delivery system comprises an outer sheath attached along the distal end of a relatively long and flexible tubular shaft. The outer sheath is capable of constraining the thin film medical device in a longitudinally stretched position, and subsequently being retracted relative to the flexible tubular shaft to release the thin film medical device from the constrained longitudinally stretched position. The delivery system further comprises an inner lumen substantially coaxial to the outer sheath, and incorporated into the flexible tubular shaft.

In still another embodiment of the invention, the delivery system is configured to deploy a thin film medical device and a mechanically expandable radial support structure. The delivery system comprises an outer sheath attached along the distal end of a relatively long and flexible tubular shaft. The outer sheath is capable of constraining the thin film medical device in a longitudinally stretched position, and subsequently being retracted relative to the flexible tubular shaft to release the thin film medical device from the constrained longitudinally stretched position. The delivery system further comprises a mechanical expansion catheter substantially coaxial too, and slideably engaged within, the outer sheath. The mechanical expansion catheter is capable of radially expanding the expandable support structure. An inner lumen substantially coaxial to the outer sheath and incorporated into the flexible tubular shaft is also provided.

DETAILED DESCRIPTION OF A PREFERRED EMBODIMENT

Figure 1A:
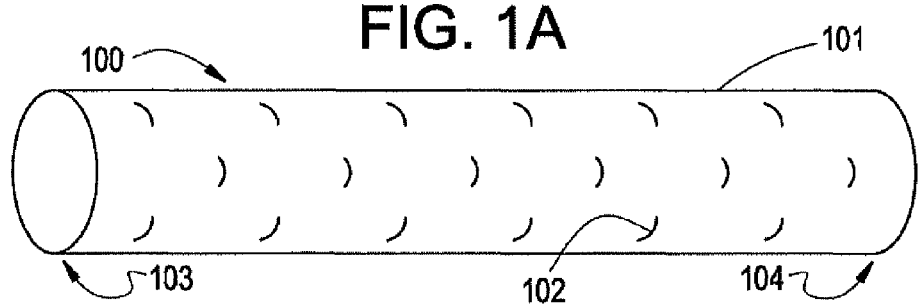
FIG. 1A show a perspective view of medical device fabricated from a thin film tube in the deployed or "pre-stretched" configuration according to one embodiment of the present invention.

The present invention discloses delivery system for a thin film medical device particularly well suited for occlusion of an aneurysm or vessel side branch, or dissection of body lumen or duct, such as an artery or vein. One advantage of the present invention is that it allows for multi-stage deployment of various members of the medical device. For example the delivery system will allow a thin film medical device to first expand independently of a supporting structure as herein disclosed. This permits the use of a thin film having different foreshortening characteristics than the support structure. In addition, it allows the thin film to be designed with a geometric pattern optimal for occluding blood, and eliminates the need to design a geometric pattern designed to have the same foreshortening properties as the supporting structure.

Although this specification provides detailed description for implantation of the medical device in a artery or vein, one of skill in the art would understand that modifications of the disclosed invention would also be well suited for use on other body lumens and anatomical passageways, such as, for example those found in the cardiovascular, lymphatic, endocrine, renal, gastrointestinal and or reproductive systems.

The primary component of the medical device is a thin film made primarily of a substantially self-supporting biocompatible metal or psuedometal. The thin film may be fabricated either as single layer, or a plurality of layers. The terms "thin film", "metal film", "thin metallic film", and "metallic thin film" are used synonymously in this application to refer to a single or plural layer film fabricated of biocompatible metal or biocompatible pseudometals having a thickness greater than 0.1 μm but less than 250 μm, preferably between 1 and 50 μm. In some particular embodiments of the invention, such as where the thin film is used as a structural support component, the thin film may have a thickness greater than approximately 25 μm. In other embodiments, for example, where the thin film is used as a cover member with additional structural support, the thin film may have a thickness of between approximately 0.1 μm and 30 μm, most preferably between 0.1 μm and 10 μm.

In a preferred embodiment, the medical device is fabricated from a shape memory thin metallic film or pseudometallic film having super elastic characteristics. One example of a shape memory metallic thin film is Nickel Titanium (Nitinol) formed into a tubular structure.

Nitinol is utilized in a wide variety of applications, including medical device applications as described above. Nitinol or NiTi alloys are widely utilized in the fabrication or construction of medical devices for a number of reasons, including its biomechanical compatibility, its bio-compatibility, its fatigue resistance, its kink resistance, its uniform plastic deformation, its magnetic resonance imaging compatibility, its ability to exert constant and gentle outward pressure, its dynamic interference, its thermal deployment capability, its elastic deployment capability, its hysteresis characteristics, and is moderately radiopacity.

Nitinol, as described above, exhibits shape memory and/or super elastic characteristics. Shape memory characteristics may be simplistically described as follows. A metallic structure, for example, a Nitinol tube that is in an Austenitic phase may be cooled to a temperature such that it is in the Martensitic phase. Once in the Martensitic phase, the Nitinol tube may be deformed into a particular configuration or shape by the application of stress. As long as the Nitinol tube is maintained in the Martensitic phase, the Nitinol tube will remain in its deformed shape. If the Nitinol tube is heated to a temperature sufficient to cause the Nitinol tube to reach the Austenitic phase, the Nitinol tube will return to its original or programmed shape. The original shape is programmed to be a particular shape by well-known techniques as briefly described above.

Super elastic characteristics may be simplistically described as follows. A metallic structure for example, a Nitinol tube that is in an Austenitic phase may be deformed to a particular shape or configuration by the application of mechanical energy. The application of mechanical energy causes a stress induced Martensitic phase transformation. In other words, the mechanical energy causes the Nitinol tube to transform from the Austenitic phase to the Martensitic phase. By utilizing the appropriate measuring instruments, one can determined that the stress from the mechanical energy causes a temperature drop in the Nitinol tube. Once the mechanical energy or stress is released, the Nitinol tube undergoes another mechanical phase transformation back to the Austenitic phase and thus its original or programmed shape. As described above, the original shape is programmed by well know techniques. The Martensitic and Austenitic phases are common phases in many metals.

Medical devices constructed from Nitinol are typically utilized in both the Martensitic phase and/or the Austenitic phase. The Martensitic phase is the low temperature phase. A material is in the Martensitic phase is typically very soft and malleable. These properties make it easier to shape or configure the Nitinol into complicated or complex structures. The Austenitic phase is the high temperature phase. A material in the Austenitic phase is generally much stronger than the materiel in the Martensitic phase. Typically, many medical devices are cooled to the Martensitic phase for manipulation and loading into delivery systems. When the device is deployed at body temperature, they return to the Austenitic phase.

Although Nitinol is described in this embodiment, it should not be understood to limit the scope of the invention. One of skill in the art would understand that other materials, both metallic and pseudo-metallic exhibiting similar shape memory and super-elastic characteristics may be used.

The tubular thin film structure is sized to match or be slightly greater than the diameter of the inner lumen of the body vessel when the tube is in the unrestrained ("self-expanded") configuration. The inherent properties of the thin Nitinol tube are such that the tube is capable of being longitudinally stretched, which decreases the tube's diameter. Reducing the diameter allows the medical device to maintain a compact profile for insertion into a body lumen via a catheter during a percutaneous, endoluminal procedure. Accordingly, the inherent shape memory and super-elastic characteristics allow the thin metallic tube to be stretched and restrained in a reduced profile configuration, and then self-expand back to its original "pre-stretched" diameter once the restraint is removed. As the tube diametrically expands, it longitudinally contracts or foreshortens to its pre-stretched length and diameter.

Figure 1B:
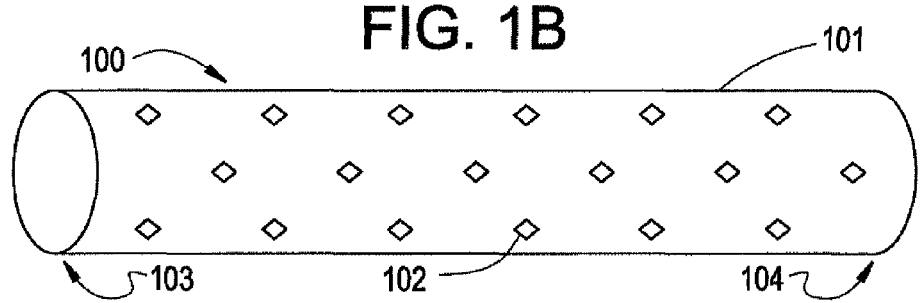
FIG. 1B shows a perspective view of a medical device fabricated from a thin film tube in the stretched reduced profile and restrained position according to one embodiment of the present invention.

FIGS. 1A and 1B show a medical device fabricated from a Nitinol thin film tube according to one embodiment of the present invention. FIG. 1A shows the thin film medical device 100 in the deployed or "pre-stretched" configuration, while FIG. 1B shows the thin film medical device 100 in the stretched reduced profile and restrained position.

To facilitate the ability for the thin film medical device 100 to stretch in the longitudinal direction, the tubular structure 101 has a plurality of radial slots 102 incised or formed circumferentially through the tube 101 wall. In one embodiment, the slots are in the form of slits made completely through the thin film tube wall 101. Alternatively, where the thin film is manufactured in layers, the radial slots 102 may be through one or more layers of the thin film tube 101 wall. As the thin film tube 101 is longitudinally stretched, the slots 102 open, creating an opening in the tube 101 wall. When the thin film tube 101 is allowed to return to the pre-stretched (radially expanded) configuration, the radial slots 102 close, excluding blood flow in the circumferential direction.

The terms exclude, excluding and variations thereof, should not be construed as having zero porosity and completely preventing fluid flow. Instead, the closed slits and apertures in the thin film that exclude fluid flow may have openings that are small enough to substantially occlude blood flow through the thin film tube 101 wall. A medical device 100 illustrating all the radial slots 102 in the open position is illustrated in FIG. 1B.

Figure 1C:
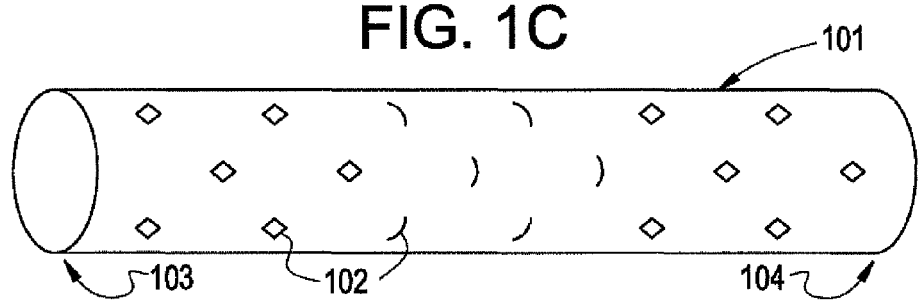
FIG. 1C illustrates a perspective view of a medical device according to one embodiment of the present invention where only a portion of the radial slots along the proximal end and distal end are open, while the radial slots in the intermediate section remain substantially closed.

The medical device 100 may also be designed so that some of the radial slots 102 can open, while other radial slots 102 remain substantially closed. FIG. 1C illustrates a medical device 100 where only a portion of the radial slots 102 along the proximal end 103 and distal end 104 are open, while the radial slots 102 in the intermediate section remain closed.

In another embodiment of the present invention, the medical device 100 may also has apertures 102 incised or formed through the tube wall in various shapes. The shapes may be chosen to facilitate longitudinal stretching and/or radial expansion of the thin film tube. Essentially, the apertures 102 in the thin film have longitudinal and latitudinal dimensions, thereby forming an opening in the thin film having a net free open area.

The above-described medical device 100 can be used, for example, across an aneurysm, side-branch vessel, or any vessel wall defect to exclude blood flow. In one embodiment of the invention, the tubular thin film 101 may be fabricated to a thickness that can support itself circumferentially. Alternatively, thinner films could be supported by a balloon or self-expanding stent or stents if additional radial support is needed.

Figure 2:
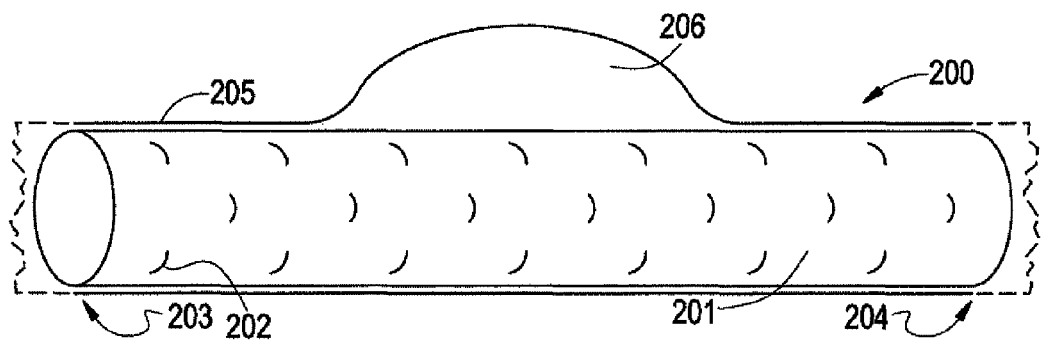
FIG. 2 is a perspective partial section view showing a medical device deployed in a vessel according to one embodiment of the present invention.

FIG. 2 is a perspective partial section view showing a medical device 200 deployed in a vessel 205 according to one embodiment of the present invention. The vessel 205 has a weakened vessel wall causing an aneurysm 206, and the medical device 200 is deployed over the aneurysm 206. The medical device 200 is self-supporting, and does not require additional stent(s) for support. As described earlier, the medical device 200 comprises a thin metallic film tube 201 having a proximal end 203 and a distal end 204. The thin film tube 201 has a series of radial slots 202 arranged circumferentially along the thin film tube 201 longitudinal axis. Upon deployment from a catheter system, the radial slots 202 incised in the thin film tube 201 substantially close, excluding blood flow in the circumferential direction. This relieves pressure in the aneurysm 206, and mitigates potential medical conditions associated with the aneurysm 206 bursting. Reducing the pressure in the aneurysm 206 may also allow the vessel 205 wall to contract.

Figure 3A:
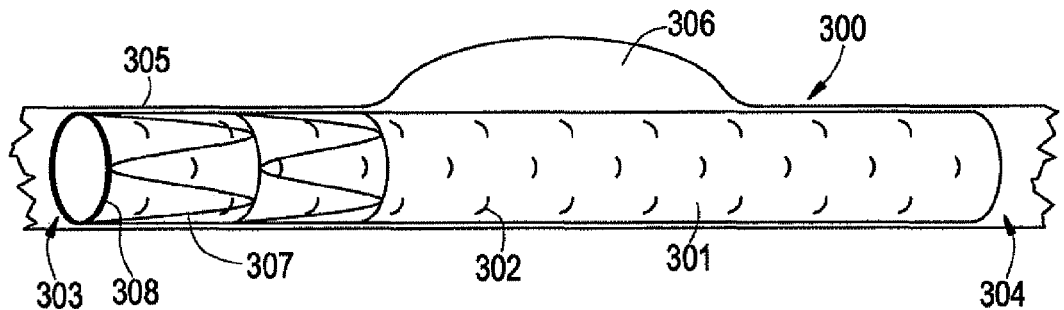
FIG. 3A is a perspective partial section view showing a medical device according to an embodiment of the present invention deployed over an aneurysm in a vessel wall, where the medical device has a proximal stent attaching the thin film tube to the vessel wall.

The medical device may also include one or more stents to assist in securing the thin film tube into the vessel wall. FIG. 3A shows a medical device 300 according to another embodiment of the present invention deployed over an aneurysm 306 in a vessel wall 305. Similar to the medical devices described above, the medical device 300 comprises a thin metallic film formed into a tube 301, having a proximal end 303 and distal end 304. The thin film tube 301 has a series of radial slots 302 incised circumferentially through the tube 301 wall. The medical device 300 additionally comprises a stent 307 along the proximal end 303.

The stent 307 disclosed comprises at least one hoop structure extending between the stent 307 proximal and distal ends, 303, 304 respectively. The hoop structure includes a plurality of longitudinally arranged strut members and a plurality of loop members connecting adjacent struts. Adjacent struts are connected at opposite ends in a substantially S or Z shaped sinusoidal pattern so as to form a plurality of cells. However, one of ordinary skill in the art would recognize that the pattern shaped by the struts is not a limiting factor, and other shaped patterns or radially expandable structures may be used.

As previously described, the stent 307 assists in anchoring the medical device 300 to the vessel 305 wall. The thin film tube 301 may be affixed to the stent 307 at anchor point 308. Attachment may be by any suitable attachment means, including adhesion resulting from radial pressure of the stent 307 against the thin metallic film tube 301, adhesion by means of a binder, heat, or chemical bond, and/or adhesion by mechanical means, such as welding or suturing between the stent 307 and the thin metallic film tube 301. It should be noted that the stent 307 does not necessarily have to be fixedly attached to the metallic film tube 301. Instead, the radially outward force that stent 307 exerts against the vessel wall may be adequate to hold the metallic thin film 301 in place.

Figure 3B:
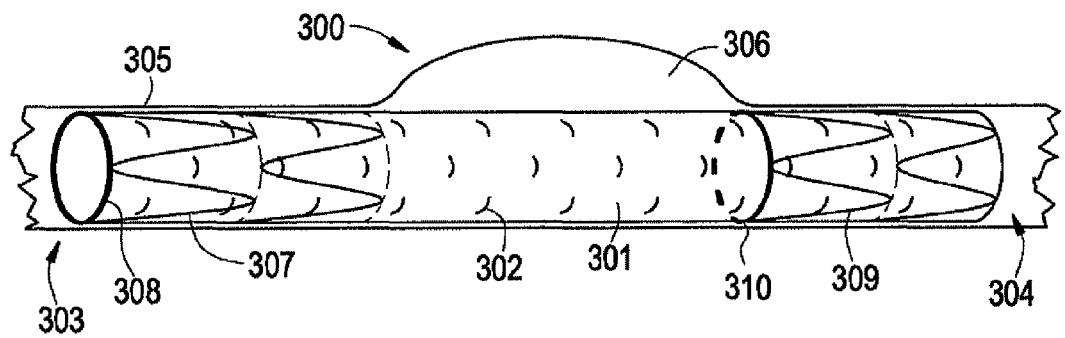
FIG. 3B is a perspective partial section view showing a medical device according to an embodiment of the present invention deployed over an aneurysm in a vessel wall, where the medical device has a proximal stent attaching the thin film tube to the vessel wall along the proximal end, as well as a distal stent attaching the distal end of the thin film tube to the vessel wall along the distal end.

In an alternate embodiment, the thin metallic film tube 301 may be anchored to the vessel 305 wall by a plurality of anchors. FIG. 3B shows a medical device 300 having a proximal stent 307 attaching the thin film tube 301 to the vessel 305 wall along the proximal end 303, as well as a distal stent 309 attaching the distal end of the thin film tube 301 to the vessel 305 wall along the distal end 304. Still one of skill in the art would understand that additional stents may be used to anchor the medical device 300 to the vessel 305 wall, such as additional proximal or distal anchors placed longitudinally along the thin film tube 301.

Figure 3C:
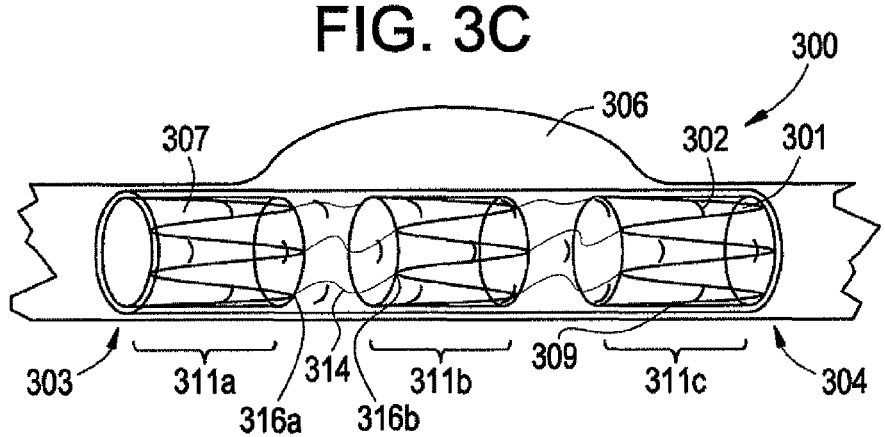
FIG. 3C is a perspective partial section view showing a medical device according to an embodiment of the present invention deployed over an aneurysm in a vessel wall, where the medical device has a stent structure having multiple hoop sections arranged axially along a central longitudinal axis.

In a further alternate embodiment, stents having multiple hoop structures or longer hoop structures may be used to fully support the thin metallic film along all or substantially all of the film's length. FIG. 3C shows a medical device 300 having a multi-hoop stent 307 supporting the metallic thin film 301 substantially along the entire length of the thin metallic film 301.

The multiple hoop stent 307 illustrated in FIG. 3C comprises three hoop structures 311A through 311C connected by a plurality of bridge members 314. Each bridge member 314 comprises two ends 316A, 316B. One end 316A, 316B of each bridge 314 is attached to one hoop. Using hoop sections 311A and 311B for example, each bridge member 314 is connected at end 316A to the proximal end of hoop 311A, and at end 316B the distal end of hoop section 311B.

Figure 4:
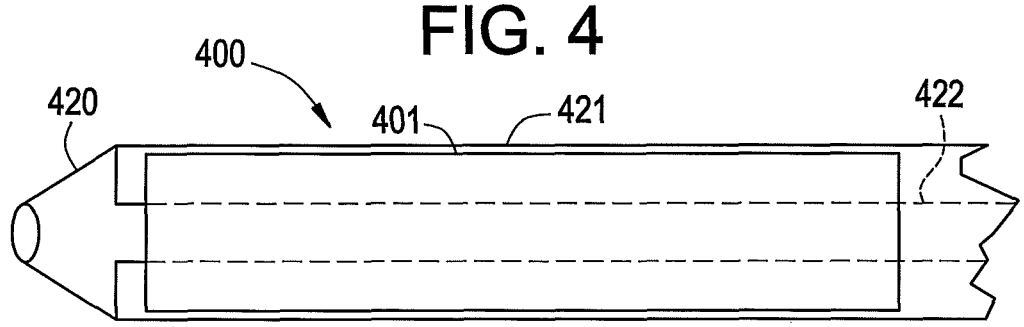
FIG. 4 is a longitudinal section view illustrating a medical device having a self-supporting metallic thin film tube loaded on a delivery catheter according to one embodiment of the present invention.

The various embodiments of the medical device described above are preferably delivered to the target area and subsequently deployed by a catheter system. FIG. 4 is a longitudinal section view illustrating a medical device 400 having a self-supporting metallic thin film tube 401 loaded on a delivery catheter 420 according to one embodiment of the present invention. The catheter 420 comprises an outer sheath 421 attached along the distal end of a relatively long and flexible tubular shaft, and an inner lumen 422. The outer sheath 421 serves to hold the thin film tube 401 in the longitudinally stretched position. The inner lumen 422 is substantially coaxial to the outer sheath 421 and provides a conduit for a guide wire.

The outer sheath 421 can be made from a variety of polymeric materials, or combination of polymeric materials, as would be understood to one of skill in the art. In a preferred embodiment of the invention, the material for the outer sheath 421 would include poly(ethylene)s, poly(amide)s, poly(urethane)s, poly(tetrafluoroethylene)s, or a combination of these materials. Other polymeric materials may also be used, including poly(carbonate)s and/or, poly(imide)s. In other embodiment of the invention the outer sheath 421 could include reinforcement materials, such as metallic braid and high tensile strength polymeric braid woven in, or onto an inner or outer surface.

The materials of construction for the inner lumen 422, sometimes called a guidewire lumen, would be obvious to those familiar with the art of balloon expandable delivery devices, PTCA devices, etc. In one embodiment of the invention, the inner lumen 422 may consist of a single polymeric material, a single polymeric material coated with a lubricious coating, or a multi-layered polymeric material. In a preferred embodiment the inner lumen 422 would be made from poly (ethylene)s, poly(amide)s, poly(urethane)s, poly(tetrafluoroethylene)s, or a combination of these materials. Other polymeric materials may also be used, including poly(carbonate)s, poly(imide)s, poly(ether, ether-ketones) etc. Embodiments of the sheath could include reinforcement materials, such as metallic braid and high tensile strength polymeric braid. Lubricious coatings could be applied to the inner surface of this tube to assist guide wire movement.

To be deployed, the medical device 400 is longitudinally stretched and mounted on the delivery catheter 420. A guide wire (not shown) is steered to the target area through well know means, and the delivery catheter 420/medical device 400 is loaded onto the guide wire using inner lumen 422. The catheter 420/medical device 400 is then pushed over the guide wire to the target site. Once properly located, the outer sheath 421 is retracted, allowing the thin film tube 401 to expand and longitudinally foreshorten to its unconstrained diameter. As previously described, this will allow the slots 402 (not shown) incised through the thin film tube 401 wall to substantially close and eliminate blood flow to the vessel wall defects.

The illustrated embodiment describes an over-the-wire delivery catheter. However, one of skill in the art would understand that other types of delivery catheters may also be used, including catheters utilizing a monorail design as are known in the art.

Figure 5:
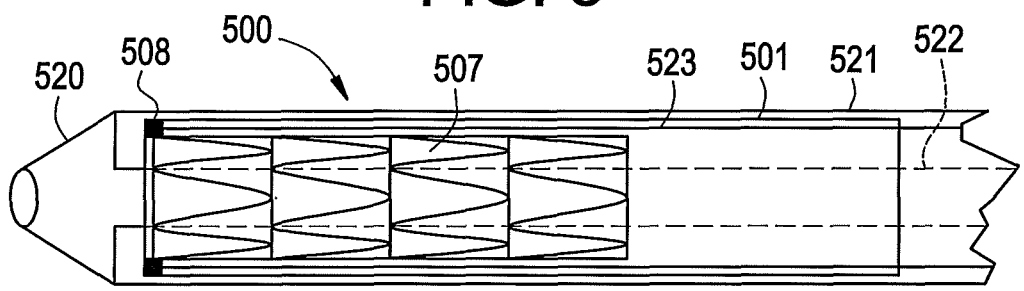
FIG. 5 is a longitudinal section view illustrating a medical device having a self-expanding stent for additional radial support according to one embodiment of the present invention.

As previously described, very thin films may require extra radial support to adequately anchor the thin film in the vessel. In one embodiment, extra radial support could be supplied by radially expandable devices, such as radially expandable stents. FIG. 5 is a longitudinal section view illustrating a medical device 500 having a self-expanding stent 507 for additional radial support according to one embodiment of the present invention.

The catheter 520 for restraining and delivering the medical device 500 having a self-expanding stent 507 has three main components. Similar to the embodiment described above, the catheter 520 comprises an outer sheath 521 that serves to hold the thin film tube 501 in the longitudinally stretched position. The outer sheath 521 can be made from various polymeric materials, or combination of polymeric materials known to one of skill in the art. In a preferred embodiment, the outer sheath 521 is constructed from poly(ethylene)s, poly(amide)s, poly(urethane)s, poly(tetrafluroethylene)s, or a combination of these materials. Still other polymeric materials may also be used for outer sheath 521, including, poly(carbonate)s and/or poly(imide)s. In addition, embodiments of the sheath could include reinforcement materials, e.g., metallic braid and high tensile strength polymeric braid.

Coaxial to the outer sheath 521 is a secondary sheath 523 of smaller diameter that serves to hold the self-expanding stent in a constrained position. Similar self-expanding stent constraining sheaths and delivery systems are found in U.S. Pat. No. 6,425,898 entitled Delivery Apparatus for a Self-expanding Stent, issued on Jul. 30, 2002 to Wilson, D. et al., which is incorporated by reference in its entirety here.

In one embodiment of the invention, the secondary sheath 523 is a composite structure incorporating an inner polytetrafluoroethylene layer, an outer polyamide layer, and a middle stainless steel braid wire layer. The outer layer can incorporate a single outer polyamide layer from proximal end to its distal end or can be a series of fused transitions decreasing in material durometer from proximal end to distal end along outer layer of the secondary sheath 523. The inclusion of transitions of varying material durometers can effectively enhance the catheter performance as it is pushed over the guidewire through the vascular anatomy. The flexibility of the delivery system from proximal end to distal end of secondary sheath 523 can improve the manner in which the system tracks over the guidewire.

The inner, outer and middle layers of secondary sheath 523 collectively enhance the stent 507 deployment. In particular, the inner layer and outer layer help to prevent the stent 507 from becoming too imbedded into the secondary sheath 523, prior to stent deployment. The middle braid layer provides radial support to the inner layer creating sufficient resistance to the outward radial force of the stent 507 within the secondary sheath 523. The inner layer also provides a low coefficient of friction surface to reduce the forces required to deploy the stent 507. In addition to the above mentioned benefit, the braid layer offers many other advantages, including providing support to give the delivery catheter 520 better pushability. Pushability is, the ability to transmit a force applied by the physician at a proximal location on the delivery catheter to the distal tip, which aids in navigation across tight stenotic lesions within the vascular anatomy. The braid layer also gives the secondary sheath 523 better resistance to elongation and necking as a result of tensile loading during sheath retraction for stent deployment.

The configuration of braid layer can be changed to change system performance. This is achieved by changing the pitch of the braid, the shape of the individual braid wires, the number of braid wires, and the braid wire diameter. Additionally, coils could be incorporated similarly to the braid layer of secondary sheath 523 to minimize stent embedment and enhance system flexibility. Use of coils in other types of catheters can be found in U.S. Pat. No. 5,279,596 issued to Castaneda et al. on Jan. 18, 1994, which is hereby incorporated herein by reference.

Alternatively, the secondary sheath 523 of the delivery catheter 520 system may comprise three tubing sections (proximal sheath, distal sheath, and distal end). The proximal sheath may be constructed of 304 stainless steel hypo-tubing (O.D.=0.065", I.D. 0.053") and be approximately 20 inches long. The proximal end of the proximal shaft is attached to a valve that provides a seal to blood flow when closed, and allows free movement over the inner member when opened. Again, the use of stainless steel for the proximal end will give the physician the necessary stiffness and column strength to manipulate the system for deployment. The distal sheath of the secondary sheath 523 may also be constructed of a co-extruded tube of nylon-12 over the PLEXAR PX209 polymer. The same logic used above applies, i.e. lubricity over the inner member (provided by the PLEXAR PX209 polymer) and the push and tracking ability of nylon-12. The distal tube is again heat fused to the distal sheath.

As earlier described, the medical device 500 may have more than one stent for added radial support, i.e. may have stent 507 and 509 (not shown) as earlier described. In each case, secondary sheath 523 may serve to hold each radially expandable stent in the constrained position.

The third component of the medical device 500 is an inner lumen 522. The inner lumen 522 is substantially coaxial to the outer sheath 521 and the secondary sheath 523, and provides a conduit for a guide wire. The thin film tube 501 is affixed to the stent 507 at anchor point 508. As earlier described, attachment may be by any suitable attachment means, including adhesion resulting from radial pressure of the stent 507 against the thin metallic film tube 501, adhesion by means of a binder, heat, or chemical bond, and/or adhesion by mechanical means, such as welding or suturing between the stent 507 and the thin metallic film tube 501.

To be deployed, the medical device 500 is longitudinally stretched (axially), restrained, and mounted on the delivery catheter 520. A guide wire (not shown) is steered to the target area through well-known means, and the delivery catheter 520/medical device 500 is loaded onto the guide wire using inner lumen 522. Alternatively, the delivery catheter 520/medical device 500 may be loaded onto the guide wire in a monorail fashion as is known in the art. The catheter 520/medical device 500 is then pushed over the guide wire to the target site. Once properly located, the outer sheath 521 is retracted, first allowing the thin film tube 501 to expand and longitudinally foreshorten to its unconstrained diameter. As previously described, this will allow the slots 502 (not shown) incised through the thin film tube 501 wall to substantially close and exclude blood flow to the vessel wall defects. The secondary sheath 523 may then be retracted, allowing the stent 507, and any other stents (not shown) to self-expand into the vessel wall (not shown). The radial pressure exerted by the stent 507 into the vessel wall anchors the stent 507 in place. As a result, the thin film tube 501 is further supported and anchored to the vessel wall.

Figure 6:
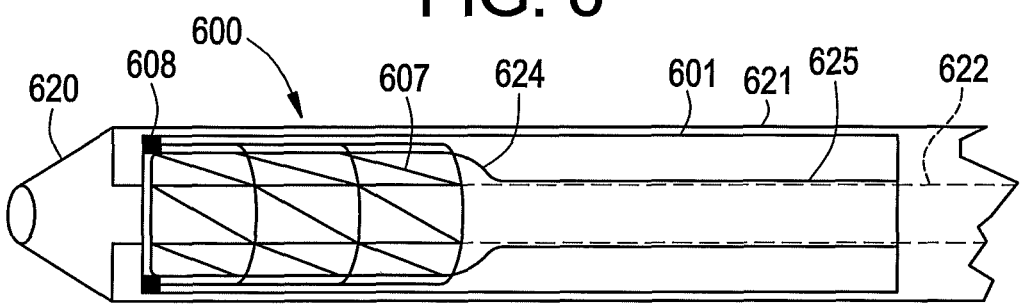
FIG. 6 is a longitudinal section view illustrating a medical device having a balloon expandable stent for additional radial support according to one embodiment of the present invention.

In an alternate embodiment, the self-expanding stent may be replaced with a balloon expandable stent. FIG. 6 is a longitudinal section view illustrating a medical device 600 having a balloon expandable stent 607 for additional radial support according to one embodiment of the present invention.

The catheter 620 for restraining and delivering the medical device 600 having a balloon expandable stent 607 has three main components. Similar to the embodiment described above, the catheter 620 comprises an outer sheath 621 that serves to hold the thin film tube 601 in the longitudinally stretched position. Coaxial to the outer sheath 621 is balloon catheter 625 having a balloon 624 mounted thereto.

The balloon catheter 625 is typical of most balloon catheters know in the art in that is has a relatively long and flexible tubular shaft defining one or more passages or lumens, and an inflatable balloon 624 attached near one end of the shaft. This end of the catheter where the balloon 624 is located is customarily referred to as the "distal" end, while the other end is called the "proximal" end. The balloon 624 is connected to one of the lumens extending through the shaft to selectively inflate and deflate the balloon 624. The other end of this inflation lumen leads to a hub coupling at the other end for connecting the shaft lumens to various equipment. Examples of this type of balloon catheter 625 are shown in U.S. Pat. No. 5,304,197, entitled "Balloons For Medical Devices And Fabrication Thereof," issued to Pinchuk et al. on Apr. 19, 1994, and also in U.S. Pat. No. 5,370,615, entitled "Balloon Catheter For Angioplasty," issued to Johnson on Dec. 6, 1994, and are incorporated herein by reference.

Various materials for the balloon catheter 625 components are well known. For example, the balloon 624 material is preferably substantially inelastic, and as such it stretches a relatively small amount under pressures of up to 15 atmospheres or more. Different balloon 624 materials may be used, including nylon, PEEK, polymer materials sold under the trade name Pebax or Plexar, polyethylene, HDPE, polyurethane, or a block copolymer thereof. Likewise, various materials may be used for the shaft components and strain relief, including for example all of the materials listed above, as well as others including metal such as a stainless steel hypotube for example. The hub may be made of a hard plastic, such as for example polycarbonate. Markers may be made of any suitably radiopaque material, metal, alloy, or combination of materials, including for example tungsten or platinum.

The balloon expandable stent 607 is mounted or crimped in a low profile configuration to the balloon catheter 625 over the expansion balloon 624. As earlier described, the medical device 600 may have more than one stent for added radial support, i.e. may have stent 607 and 609 (not shown), and possible others, as earlier described. In each case, each balloon 624 or balloons 624, on the balloon catheter 625 may serve to hold and deliver each radially expandable stent in the constrained position.

The third component of the medical device 600 is an inner lumen 622. The inner lumen 622 is substantially coaxial to the outer sheath 621 and the balloon catheter 625, and provides a conduit for a guide wire. In a preferred embodiment, the inner lumen 622 is an integral part of the balloon catheter 625. Alternatively, the catheter 620 may be a loop or similar capture device along the distal end to accept the guide wire in a monorail fashion. Monorail type catheters are known in the art.

The thin film tube 601 is preferably affixed to the stent 607 at anchor point 608. As earlier described, attachment may be by any suitable attachment means, including adhesion resulting from radial pressure of the stent 607 against the thin metallic film tube 601, adhesion by means of a binder, heat, or chemical bond, and/or adhesion by mechanical means, such as welding or suturing between the stent 607 and the thin metallic film tube 601.

To be deployed, the medical device 600 is mounted on the balloon catheter 625. A guide wire (not shown) is steered to the target area through well know means, and the balloon catheter 625/medical device 600 is loaded onto the guide wire using inner lumen 622. The catheter 625/medical device 500 is then pushed over the guide wire to the target site. Once properly located, the outer sheath 621 is retracted, first allowing the thin film tube 601 to expand and longitudinally foreshorten to its unconstrained diameter. As previously described, this will allow the slots 602 (not shown) incised through the thin film tube 601 wall to substantially close and exclude blood flow to the vessel wall defects. The balloon 624 is then inflated (expanded), expanding the stent 607, and any other stents (not shown) into the vessel wall (not shown). The radial pressure exerted by the stent 607 into the vessel wall anchors the stent 607 in place. As a result, the thin film tube 601 is further supported and anchored to the vessel wall.

While a number of variations of the invention have been shown and described in detail, other modifications and methods of use contemplated within the scope of this invention will be readily apparent to those of skill in the art based upon this disclosure. It is contemplated that various combinations or sub combinations of the specific embodiments may be made and still fall within the scope of the invention. Moreover, all assemblies described are believed useful when modified to treat other vessels or lumens in the body, in particular other regions of the body where fluid flow in a body vessel or lumen needs to be excluded or regulated. This may include, for example, the coronary, vascular, non-vascular and peripheral vessels and ducts. Accordingly, it should be understood that various applications, modifications and substitutions may be made of equivalents without departing from the spirit of the invention or the scope of the following claims.

The following claims are provided to illustrate examples of some beneficial aspects of the subject matter disclosed herein which are within the scope of the present invention.

What is claimed is:

1. A delivery system for deploying a tubular thin film and a mechanically expandable stent, the system includes the tubular thin film and the stent prior to their deployment, the tubular thin film including a self-supporting biocompatible metal or pseudometals of a thickness from between 1 micron and 250 microns, and further comprising:
   a long and flexible tubular shaft having proximal and distal ends and defining an inner lumen there through;
   a retractable, tubular outer sheath attached along the distal end of the long and flexible tubular shaft and configured to extend along the length of the tubular thin film, the outer sheath being configured to constrain the tubular thin film in a longitudinally stretched position having a constrained length $L_1$ and a constrained diameter $D_1$ prior to delivery completion, and subsequently being retracted relative to the flexible tubular shaft to release the thin film from the constrained longitudinally stretched position to a longitudinally relaxed position having a length $L_2$ and a diameter $D_2$, wherein $L_1$ is longer than $L_2$ and $D_1$ is smaller than $D_2$;
   a mechanical expansion catheter substantially coaxial to, and slideably engaged within, the outer sheath, the mechanical expansion catheter comprising the mechanically expandable stent coaxially mounted on a radially expandable expansion member, the expansion member being configured to mechanically expand the expandable stent by generation of a radially directed force; and
   a secondary sheath disposed next to the stent to surround the stent, the secondary sheath comprising a composite structure incorporating an inner layer, an outer layer, and a middle layer, such that the inner layer and outer layer help to prevent the stent from becoming too imbedded into the secondary sheath prior to stent deployment, the secondary sheath being of a smaller diameter than the outer sheath and coaxial thereto with the thin film surrounding the secondary sheath, the secondary sheath serving to hold the stent in a constrained position.

2. The delivery system of claim 1 wherein the outer sheath comprises a polymeric material.

3. The delivery system of claim 2 wherein the polymeric material comprises a polymer from the group consisting of polyethylene, polyamide, polyurethane, and polytetrafluroethylene.

4. The delivery system of claim 2 wherein the polymeric material comprises a polymer from the group consisting of polycarbonate and polyimide.

5. The delivery system of claim 1 wherein the outer sheath has reinforcement material.

6. The delivery system of claim 5 wherein the reinforcement material is a metallic braid integrated into the outer sheath.

7. The delivery system of claim 5 wherein the reinforcement material is a high tensile strength polymeric braid woven into the outer sheath.

8. The delivery system of claim 1 wherein the long and flexible tubular shaft comprises a multi-layered polymeric material.

9. The delivery system of claim 1 wherein the long and flexible tubular shaft comprises a reinforcement material.

10. The delivery system of claim 9 wherein the reinforcement material is a metallic braid integrated into the inner lumen.

11. The delivery system of claim 9 wherein the reinforcement material is a high tensile strength polymeric braid woven into the inner lumen.

* * * * *